United States Patent [19]

Free

[11] Patent Number: 4,753,636
[45] Date of Patent: Jun. 28, 1988

[54] SUBCUTANEOUS IMPLANT KIT
[75] Inventor: Michael J. Free, Seattle, Wash.
[73] Assignee: Endocon, Inc., Boston, Mass.
[21] Appl. No.: 836,089
[22] Filed: Mar. 4, 1986

Related U.S. Application Data
[63] Continuation of Ser. No. 519,548, Aug. 2, 1983.
[51] Int. Cl.⁴ .................. A61M 31/00; A61M 5/18
[52] U.S. Cl. ............................. 604/49; 604/60; 604/115; 604/891.1
[58] Field of Search ............. 604/51, 57, 22, 59–64, 604/47, 48, 891, 896, 49, 115

[56] References Cited
U.S. PATENT DOCUMENTS

| | | | |
|---|---|---|---|
| 2,009,393 | 7/1935 | Failla | 604/60 |
| 2,269,963 | 1/1942 | Wappler | 604/61 |
| 2,646,799 | 7/1953 | Jacoby, Jr. | 128/314 |
| 3,439,675 | 4/1969 | Cohen | 604/192 |
| 3,590,816 | 7/1971 | Rosenthal | 604/16 |
| 4,147,164 | 4/1979 | Behney | 604/60 |
| 4,438,770 | 3/1984 | Jnger et al. | 128/305 |
| 4,451,253 | 5/1984 | Harman | 604/60 |

Primary Examiner—Stephen C. Pellegrino
Attorney, Agent, or Firm—Wolf, Greenfield & Sacks

[57] ABSTRACT

A presterilized, packaged, subcutaneous contraception kit including a simple, disposable cutter device (1) which makes precise, repeatable less than 5 mm incisions in the skin which is capable of being used by nonskilled personnel. The contraceptive steroid delivery systems are preloaded in a disposable flexible plastic carrier (30) which is used to blunt disect under the skin where the capsules (52) are deposited by the operation of drawing the carrier (30) back over a rod (42) which is held relatively stationary. The carrier (30) stops automatically when one capsule has been deposited and must be triggered in order to deposit the next capsule.

14 Claims, 2 Drawing Sheets

SUBCUTANEOUS IMPLANT KIT

This application is a continuation of U.S. patent application Ser. No. 519,548, filed Aug. 2, 1983, now abandoned.

TECHNICAL FIELD

The present invention relates to the subcutaneous implantation of slow discharge medicines and in particular a prepackaged sterile kit including all of the elements necessary for such an implant in a form capable of nonclinical use by relatively unskilled personnel while minimizing the danger to the recipient.

BACKGROUND ART

It has been established and understood by the modern world as well as by the emerging countries, that it has become necessary to provide some sort of birth control to limit population growth.

Even in situations where the prospective mother is in full agreement that she should refrain from childbirth for at least a limited period of time, the fact is often not easily accomplished. In many regions of the world and for many individuals in other regions, the utilization of a mechanical device, such as a barrier, is unsatisfactory. The requirement of ingesting an oral contraceptive on a daily basis often does not fit into an acceptable ritual for the individual involved, particularly in a nonstructured living situation, Further, because of nutritional or health problems, predisposing anemia or diseases of the reproductive tract an intrauterine device may not be advisable in many cases.

To resolve these problems, there have been developed contraceptive steriod delivery systems requiring subcutaneous implant which, when properly administered, can provide contraception for several years. The removal and replacement of the implant may be accomplished on an outpatient basis or even in the field.

It is to be understood that although the particular instruments developed and described herein were primarily developed for utilization with contraceptives in the Third World and other emerging countries, the devices may equally be as well used for any other type of a subcutaneous system.

Historically, subcutaneous delivery systems have required the utilization of a scalpel to make an incision and a large metal trocar for placing the capsule. Prior methods have also required that each capsule be handled individually thereby greatly increasing the risk of contamination. Further, the safety of the procedure depends upon the local sterilization practices and preparation of the material.

Apparatus known to the present inventor utilized for various specialized cuts include U.S. Pat. No. 3,631,858 granted Jan. 4, 1972 to Ersek, which discloses a means for simultaneously clamping and severing the umbilical cord of a newly born infant. This device includes, as a portion thereof, a fixed blade 20 secured to a jaw such that when the jaws are closed the blade 20 slices the umbilical cord and it is clamped by the side portions of the jaw.

U.S. Pat. No. 3,302,308, granted June 6, 1967 to Hurley, is particularly designed for use in clamping or cutting an umbilical cord and/or clamping and cutting arteries or veins in surgical operations and includes a fixed blade surrounded by holding or clamping means.

U.S. Pat. No. 2,288,445 granted June 30, 1942 to Frizzell, discloses a device for marking the ear of an animal by making an incision therein and includes a pair of jaws for holding the flesh portion and relatively movable blade such that once the flesh is in position, the blade can be activated, making the desired cut.

U.S. Pat. No. 2,646,799 granted July 28, 1953 to Jacoby, discloses a blood lencet wherein a pointed knife is mounted on a resilient arm which is separately activated following the pinching of a limited amount of tissue between a pair of jaws. The jaws are spring biased outwardly.

Prior art known to the inventor which deal with the subcutaneous placement of drugs or the sterile packaging of drugs include:

U.S. Pat. No. 2,513,014 granted June 27, 1950 to Fields, which discloses a tubular needle member including a handle portion and an enlarged coaxial chamber such that a prepackaged additional tube can be placed in the enlarged coaxial chamber and a plunger utilized to push the medicinal capsule out of the prepackaged capsule, through the needle, to its resting place beneath the skin.

U.S. Pat. No. 3,402,712 granted Sept. 24, 1968 to Eisenhand, discloses a multiple pellet implanter wherein a hypodermic needle 27 is placed beneath the skin of the receiving animal and one or more pellets are introduced by activating the trigger which allows a new pellet to drop within a chamber and activate a plunger to discharge the pellet to the proper position.

U.S. Pat. No. 4,086,914 granted May 2, 1978 to Moore, discloses an implant injector including a means to interact between the inner injection carrying member and the plunger such that the plunger must be manipulated specifically to move in predetermined, spaced advances, implanting individual capsules.

U.S. Pat. No. 4,263,910 granted Apr. 28, 1981 to Pardekooper et al, discloses a sterile packaging means such that an implant tool individually penetrates a sealed cell, picking up the implantee, carrying it, without need to have human contact, to be placed within the animal by means of the sharpened tool.

With the above noted prior art and problems in mind, it is an object of the present invention to provide a presterilized packaged including a nonthreatening means for incising the flesh and a sterile, relatively flexible means for implanting one or more implantates beneath the skin.

It is another object of the present invention to provide an implant mechanism which is simple to operate and includes a means whereby the operator necessarily must perform a separate physical step for each implant, thus preventing the inadvertent implantation of more than one capsule.

Still a further object of the present invention is to provide an incisor whereby the operator need not necessarily be skilled. The configuration of the instrument is such that a predetermined amount of flesh is pinched between two blunt, jaw-like elements and, upon application of a predetermined amount of pressure, a blade swings across the captured flesh and causes a precise incision.

Yet another object of the present invention is to provide a presterilized package for a subcutaneous inplant containing the cutter, the implanter, and the implantate such that the entire apparatus may be transported to and easily stored at remote locations without affecting the sterility.

BEST MODE FOR CARRYING OUT THE INVENTION

Figure 1:
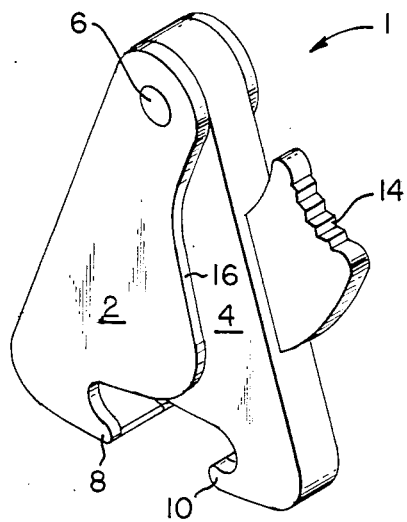
FIG. 1 is an isometric view of the inventive cutter.

As seen in FIG. 1, the cutter or incisor includes a pair of legs 2, 4, pivotally secured together as at 6. The outermost portion of each leg terminates in an inwardly projecting foot 8, 10, adapted to oppose each other and as explained hereinafter, grip a substantially predetermined amount of the flesh to be incised. Located on the outer surfaces of legs 2, 4, are handle or gripper-type members 12 and 14, with gripper 14 also serving as the actuator for the cutting blade, as described hereinafter.

Figure 2:
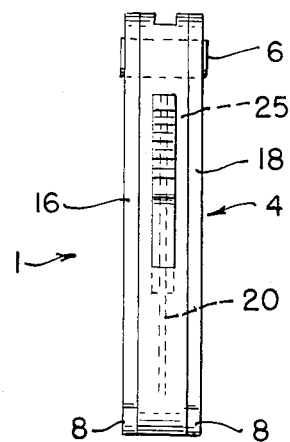
FIG. 2 is a side view of the cutter of FIG. 1.

Referring now to FIG. 2, it can be seen that each leg member is essentially a hollow shell having side walls 16, 18, between which is mounted the blade 20, held in position by means of detent 22.

Figure 3:
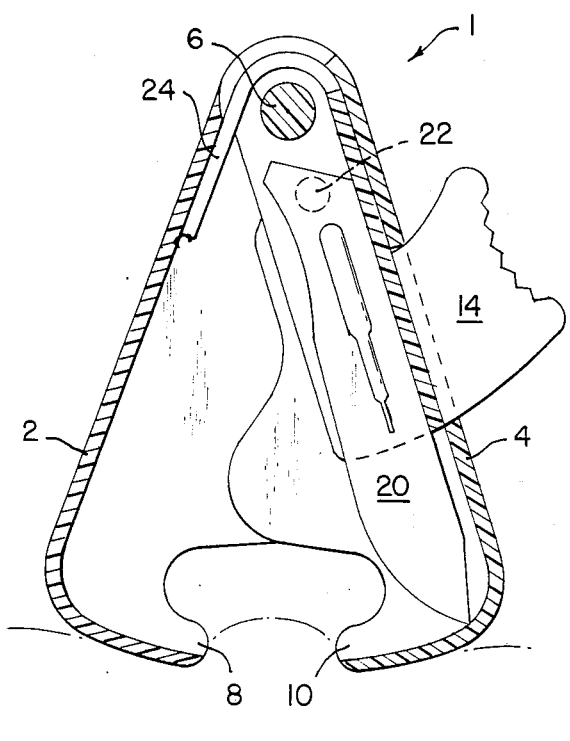
FIG. 3 is a sectional view depicting the relationship of the cutting blade and the gripper portion.
Figure 4:
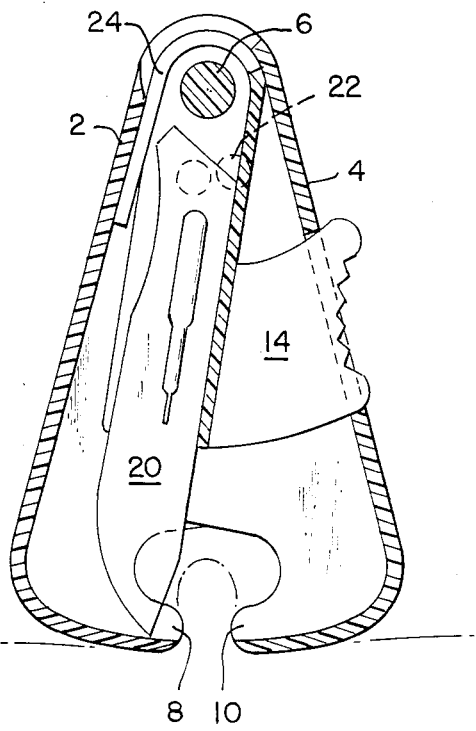
FIG. 4 is a sectional view of the cutter of FIG. 1 depicting the relationship of the cutter itself and the gripped flesh.

As seen in FIG. 3, the jaws 2, 4, are urged to an open position by means of spring member 24 which, in combination with detent 22, serves to hold the blade 20 in its ready position, totally enclosed within jaw member 4.

In operation, the cutter is placed adjacent to the skin, which, in the case of the contraceptive implant, may be either the inner part of the arm above or below the elbow, or the gluteal region, and the operator squeezes the two handles, causing the legs 8, 10, to move toward each other causing the feet to pinch a small portion of skin therebetween. Upon the application of a predetermined amount of pressure, the frictional resistance of the detent is overcome and the blade 20 swings about its pivot point to be arrested by the interior surface of the other leg member, while the blade moves from one leg to the other, it slices through the skin pinched between the feet. It is to be understood that the incision is controlled as to its length and depth because only a predetermined amount of skin may be pinched prior to the cut.

Figure 5:
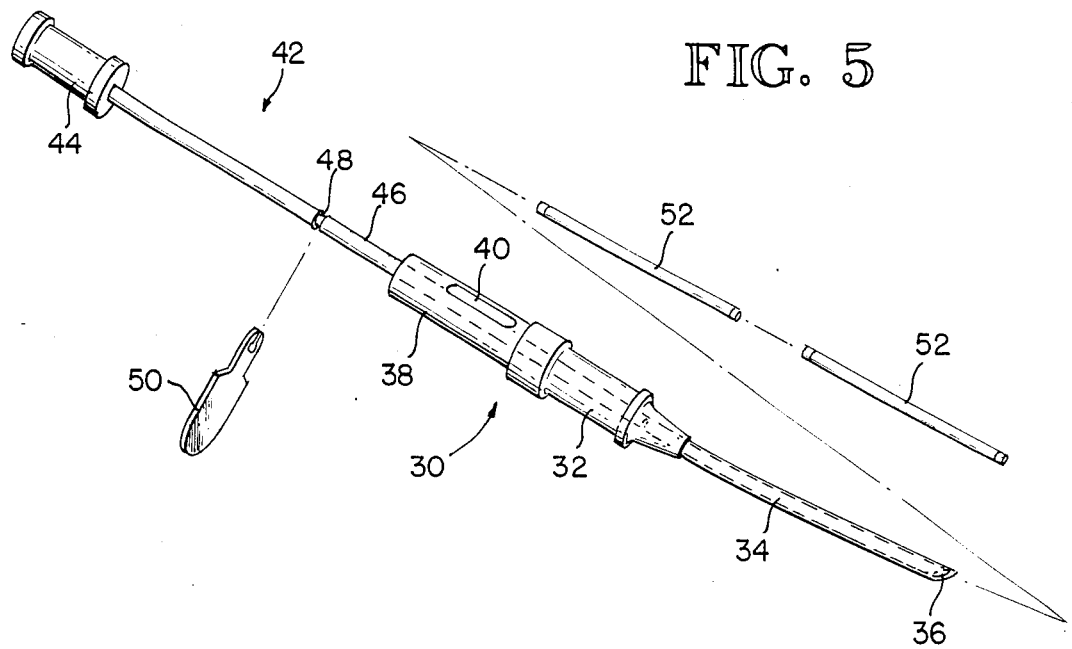
FIG. 5 is an isometric view of the implanter device with the plunger in operating position.

The companion element to the slicer is shown in FIG. 5 wherein there is disclosed a subcutaneous deposit mechanism having a hollow main body portion 30, including a gripping surface 32, and then necking down into a smaller diameter needle-like nose portion 34, having a flexible diagonally cut, smoothly polished end 36 without a cutting edge. The device may be placed within the incision and then used for blunt dissecting to the proper location for the implantate when preparing to make the implant. Unlike cutting needle, the mechanism maintains proper depth without operator skill.

Figure 8:
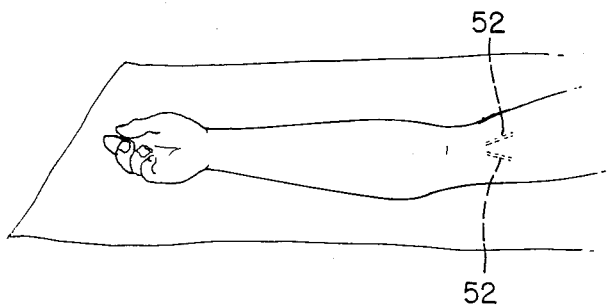
FIG. 8 is a view showing the recommended placement of the contraceptive implants.

The rearwardmost portion of the inserting tool 38 includes an orientation disclosing element 40 such that the operator will always know the relative placement of the slant surface 36 during operation of placing the nose in position. A plunger 42 is provided, having a handle portion 44 and a shaft portion 46, which is of a diameter to fit within the nose portion 34 and includes a groove 48 into which a tab element 50 may be placed. When inserting the implant, such as seen in the upper portion of this view and designated as 52, two or more of the implants (depending upon design) may be loaded within the chamber and the operator, after locating the nose properly and retaining the plunger relatively stable while withdrawing the carrier mechanism, will know when one is appropriately implanted because the rear portion of the inserter mechanism tool 38 will abut against the tab 50. The operator will then move the insert device to another location, remove the tab, and deposit the second implant. It is to be noted at this point that when used for a contraceptive means, the present state of the art of steroid implants utilizes 2 or 6 implants which are placed in a fan-like configuration as shown in FIG. 8.

Figure 6:
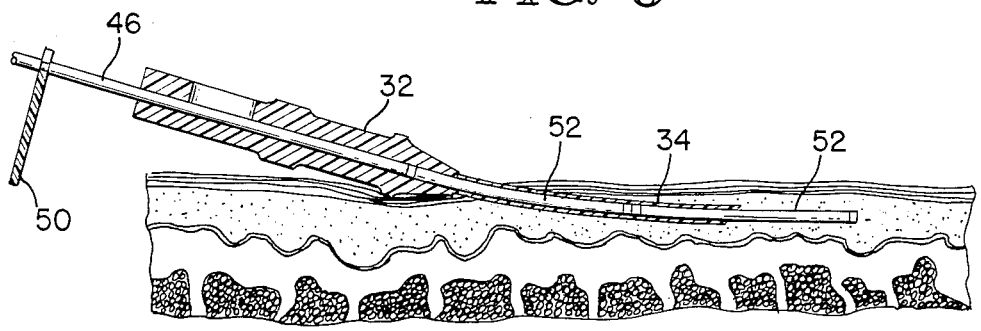
FIG. 6 is a sectional view showing the implanter in operation.

Referring to FIG. 6, the needle portion of the implant device is shown beneath the skin and the first implant implant 52 has been partially placed in position. In operation, once the implant device has been properly located, it is partially retracted while holding the plunger stationary thus leaving implantate in position. The device can then be moved slightly, using the same incision, and pushed forward to locate the second device.

Figure 7:
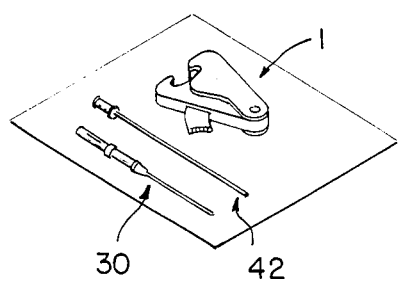
FIG. 7 is a view of a package including the cutter, the implanter, and the implantate.

As seen in FIG. 7, the instruments, i.e. the cutter, the implant device with the inplant within its chamber, and the plunger may all conveniently be placed in a sterile bubble package or the like for transport and storage.

Thus, as can readily be seen, the present invention provides a safe, sterile insertion mechanism for providing long-term inplantable contraception to those people who do not readily come into contact with physicians and/or whose lives are not structured and therefore, other acceptable methods of birth control are not applicable. Further, since the devices are not forbidding in appearance and preferably largely made of plastic or other disposable material, are not threatening and because of the low cost may be discarded after use.

I claim:

1. Apparatus for subcutaneously placing a medicinal implant beneath the skin through an incision made through the skin, comprising:
   an implanter for inserting the implant through the incision and for locating the implant beneath the surface of the skin and having a bore within which the implant is initially contained, including:
   a hollow main body portion forming a first part of the bore; and
   insertion means, connected to the main body portion to form a second part of the bore, and adapted to be inserted through the incision and beneath the skin, including:
     means for blunt dissecting cutaneous tissues when inserted beneath the skin through said incision; and
     a long, hollow, needle-like means, which is flexible along its entire length, for flexibly connecting the hollow main body portion to the blunt dissecting means so that the insertion means may flex along its entire length when inserted through said incision; and
   manually-activated means, located within the bore and operable when the insertion means has been inserted through an incision, for ejecting an implant out from the main body portion through said insertion means and into a location under the surface of the person's skin.

2. The apparatus of claim 1 wherein the first end of the insertion means includes a diagonally-cut, smoothly-polished end without a cutting.

3. The apparatus of claim 2 wherein the insertion means further includes means for determining the orientation of the diagonally-cut end.

4. The apparatus of claim 3 wherein the orientation-determining means is constructed so that the diagonally-cut end of the insertion means is inserted through the incision with the slant edge thereof facing towards the skin.

5. The apparatus of claim 3 wherein the means for ejecting includes a manually-operable plunger which is adapted to slide within said body portion and insertion means.

6. The apparatus of claim 5 wherein the implanter bore is long enough to contain a plurality of implants in and end-to-end relationship;

and wherein the plunger has a portion which extends proximally beyond the main body portion, the plunger including one or more notches and an equal number of associated tabs which are engagable with the notches, the notches being located on the plunger so that said tabs when engaged with the associated notches will contact the body portion to prevent further distal movement of the plunger after one of the plurality of implants is located beneath the skin, the tabs being disengagable from the notch to allow a next implant to be located beneath the skin.

7. The apparatus of claim 3 wherein the insertion means is made of plastic.

8. A kit for subcutaneously placing a medicinal implant beneath the skin, comprising:
cutter means for making an incision of a controlled length and depth in the skin;
an implanter for inserting the implant through the incision and for locating the implant beneath the surface of the skin and having a bore within which the implant is initially contained, including;
a hollow main body portion forming a first part of the bore; and
insertion means, connected to the main body portion to form a second part of the bore and adapted to be inserted through the incision and beneath the skin, including:
means for blunt dissecting cutaneous tissues when inserted beneath the skin through said incision: and
a long, hollow, needle-like means which is flexible along its entire length, for flexibly connecting the hollow main body portion to the blunt dissecting means so that the insertion means may flex along its entire length when inserted through said incision; and
manually-activated means, located within the bore and operable when the insertion means has been inserted through an incision, for ejecting an implant out from the main body portion through said insertion means and into a location under the surface of the person's skin.

9. The apparatus of claim 8 wherein the cutter means further includes means for limiting the incision to five millimeters or less.

10. The apparatus of claim 8 wherein the main body portion further includes means for containing within the hollow part thereof a plurality of elongate implants located in line with one another; and
wherein the means for ejecting includes means for determining when each one of the plurality of implants has been completely ejected from the insertion means.

11. A method of subcutaneously placing a medicinal implant beneath the skin, including the steps of:
making an incision of a predetermined length and depth in the skin;
blunt dissecting the tissue beneath the skin surface by inserting a first end of a long, hollow, substantially-uniformly flexible, needle-like instrument into the incision and pushing it through the cutaneous tissues along its axis while allowing the instrument to flex so that it follows a path generally parallel with the surface of the skin, said first end being formed as a blunt end without a cutting edge;
inserting an implant into the second end of the instrument and pushing it through the hollow portion of the instrument until the implant come to a first position at the first end of the instrument; and
maintaining the implant in said first position while retracting the instrument so that the implant remains at said first position when the hollow instrument has been retracted sufficiently far so that it no longer surrounds the implant.

12. The method of claim 11 wherein said first end of the instrument has a diagonally-cut, smoothly polished end forming a bevel, and further including the step of:
inserting the instrument into the incision with an orientation wherein the bevel faces the skin as it is inserted, and maintaining that orientation as the instrument blunt dissects the tissue beneath the skin surface.

13. The method of claim 11 further including the steps of;
after the instrument has been retracted sufficiently far so that it no longer surrounds the implant, moving the instrument while maintaining it within the incision;
blunt dissecting the tissue beneath the skin surface by again pushing the instrument through the cutaneous tissues as aforeside so as to locate the first end of the instrument at a second position generally alongside said first position;
repeating the aforesaid steps of inserting an implant and retracting the instrument to locate a second implant at said second position.

14. The method of claim 13 wherein said step of moving the instrument after it has been retracted the first time includes the step of pivoting it about an axis perpendicular to the surface of the skin so that the implants at said first and second position are inserted in a fan-like pattern.

* * * * *

UNITED STATES PATENT AND TRADEMARK OFFICE
CERTIFICATE OF CORRECTION

PATENT NO. : 4,753,636

DATED : June 28, 1988

INVENTOR(S) : Michael J. Free

It is certified that error appears in the above-identified patent and that said Letters Patent is hereby corrected as shown below:

Claim 2, column 5 line 5 after --cutting-- insert "edge".

Signed and Sealed this

Third Day of January, 1989

Attest:

DONALD J. QUIGG

*Attesting Officer*  *Commissioner of Patents and Trademarks*